United States Patent [19]
Slater et al.

[11] Patent Number: 5,385,564
[45] Date of Patent: Jan. 31, 1995

[54] SYSTEM FOR PREPARATION AND USE OF DIALYSIS SOLUTION

[75] Inventors: Glenn L. Slater, Ogdon, Utah; Jerry Woods, Pittsburg, Calif.; Steve Alford, Antioch, Calif.; Dave Updyke, Pittsburg, Calif.; Rick Methe, Antioch, Calif.

[73] Assignee: Fresenius USA, Inc., Walnut Creek, Calif.

[21] Appl. No.: 957,050

[22] Filed: Oct. 5, 1992

[51] Int. Cl.$^6$ .......................... A61B 19/00; A61M 5/32
[52] U.S. Cl. ...................... 604/416; 604/403; 604/82; 604/83; 604/84; 604/56; 604/85; 128/898
[58] Field of Search ....................... 128/898, DIG. 24; 604/49, 56, 82-85, 403, 416

[56] References Cited

U.S. PATENT DOCUMENTS

| | | | |
|---|---|---|---|
| 2,800,269 | 7/1957 | Smith | 128/DIG. 24 |
| 4,282,863 | 8/1981 | Biegler et al. | 604/89 |
| 4,664,891 | 5/1987 | Cosentino et al. | |
| 5,071,558 | 12/1991 | Itoh | |

Primary Examiner—Randall L. Green
Assistant Examiner—P. Zuttarelli
Attorney, Agent, or Firm—Beaton & Swanson

[57] ABSTRACT

A system for packaging and using granulated solid dialysate concentrate. A bag is constructed to hold granulated or powder concentrate, having a V-shaped bottom with an access port in the bottom. Water is flowed through the access port and into the bag using suitable water control means. The incoming water lifts and suspends the granules or powder in a turbulent flow, thereby filling the container simultaneous with dissolving the granules or powder. The water with dissolve concentrate then constitutes the dialysis solution and is ready for use or transfer to a dialysate delivery machine.

7 Claims, 3 Drawing Sheets 5,385,564

SYSTEM FOR PREPARATION AND USE OF DIALYSIS SOLUTION

FIELD OF THE INVENTION

The present invention relates to the field of dialysis. In particular, the invention relates to the packaging of granulated solid dialysate concentrate in a compact container, mixing the concentrate to form a dialysis solution in the container, and using the dialysis solution from the container.

BACKGROUND OF THE INVENTION

The common treatment for renal failure is hemodialysis treatment or peritoneal dialysis treatment. Both treatments utilize the diffusion of liquid through a semipermeable membrane. In the case of hemodialysis the membrane is in a dialyzer external to the patient, so that blood is withdrawn from the patient's vascular system and passed across the membrane while dialysis solution is passed across the other side of the membrane. Impurities in the blood are drawn through the membrane by osmotic pressure on the membrane and are disposed of in the discarded dialysis solution. In the case of peritoneal dialysis, the semipermeable membrane is the patient's peritoneal membrane. Dialysis solution is introduced into and retained for a period of time in the peritoneal cavity, and impurities in the blood migrate through the peritoneal membrane and into the dialysis solution. The dialysis solution with the impurities is then withdrawn from the peritoneal cavity and discarded.

Both hemodialysis and peritoneal dialysis require significant amounts of dialysis solution, sometimes called dialysate. Common dialysates are primarily water, but with low ionic concentrations of dissolved sodium, potassium, calcium, magnesium, chloride, acetate, glucose and bicarbonate. The proportions of these and other compounds depends on a variety of factors. Regardless of the exact concentrations and relative proportions of the dissolved compounds, the main material in all dialysates is water.

Dialysis solutions have in the past been premixed and prepackaged in a variety of mixes and sizes, so that the patient or the medical professional simply selects the desired size and mix of dialysate, makes the appropriate tubing connections to the prepackaged dialysates and to the patient and the dialysis machine, and then commences the procedure.

Although this practice of prepackaging dialysate was convenient, it was somewhat expensive and cumbersome. Effective dialysis treatment generally requires several dialysis sessions per week, and each session requires at least several liters (and perhaps several dozen liters) of dialysate. Therefore, a single patient could go through hundreds of liters of dialysate a month. Multiplied by a number of dialysis patients, a single dialysis facility would use many thousands of liters of solution a month. This large quantity of dialysate was expensive and inconvenient to store, and was also expensive to ship from a manufacturing plant to dialysis facilities throughout the world.

The expense and inconvenience of shipping and storing large quantities of dialysis solution was partially overcome by the introduction and widespread acceptance of granulated solid dialysate concentrate. Such concentrates are simply dry mixes in solid granulated form, which are dissolved in water at the treatment site and then the water with the dissolved ions becomes the dialysate to be administered to the patient. This greatly reduces the volume and especially the weight of the material that is shipped from manufacturing plants to dialysis treatment facilities, thereby reducing the cost of shipping and the cost and inconvenience of storage. For purposes of the claims herein, "granulated" is intended to include powders or any other loose solid form.

A drawback to the use of dialysate concentrates is that they are not conveniently prepackaged and ready for use. While prepackaged liquid dialysate could simply be attached to the tubing set and used, dialysate concentrate must be measured and mixed with water. This requires a measurement system for both the dialysate concentrate and the water, a mixing system which ensures complete dissolving of the concentrate in the water, and a storage container for the dialysate once the measurement and mixing is completed so that the dialysate can then be used. Manufacturers commonly package the concentrate in small fix-sized packages to assist in the measurement process, but the treatment facilities often open the small packages and combine them into large containers, thereby once again requiring the measurement process.

Accordingly, there is a need for a system for packaging and using dialysate concentrate which preserves the advantages of dialysate concentrate in reducing shipping and storing costs, but also is simple to use and requires little or no measurement, mixing or transfer to a separate container.

DESCRIPTION OF THE PREFERRED EMBODIMENT

Figure 1:
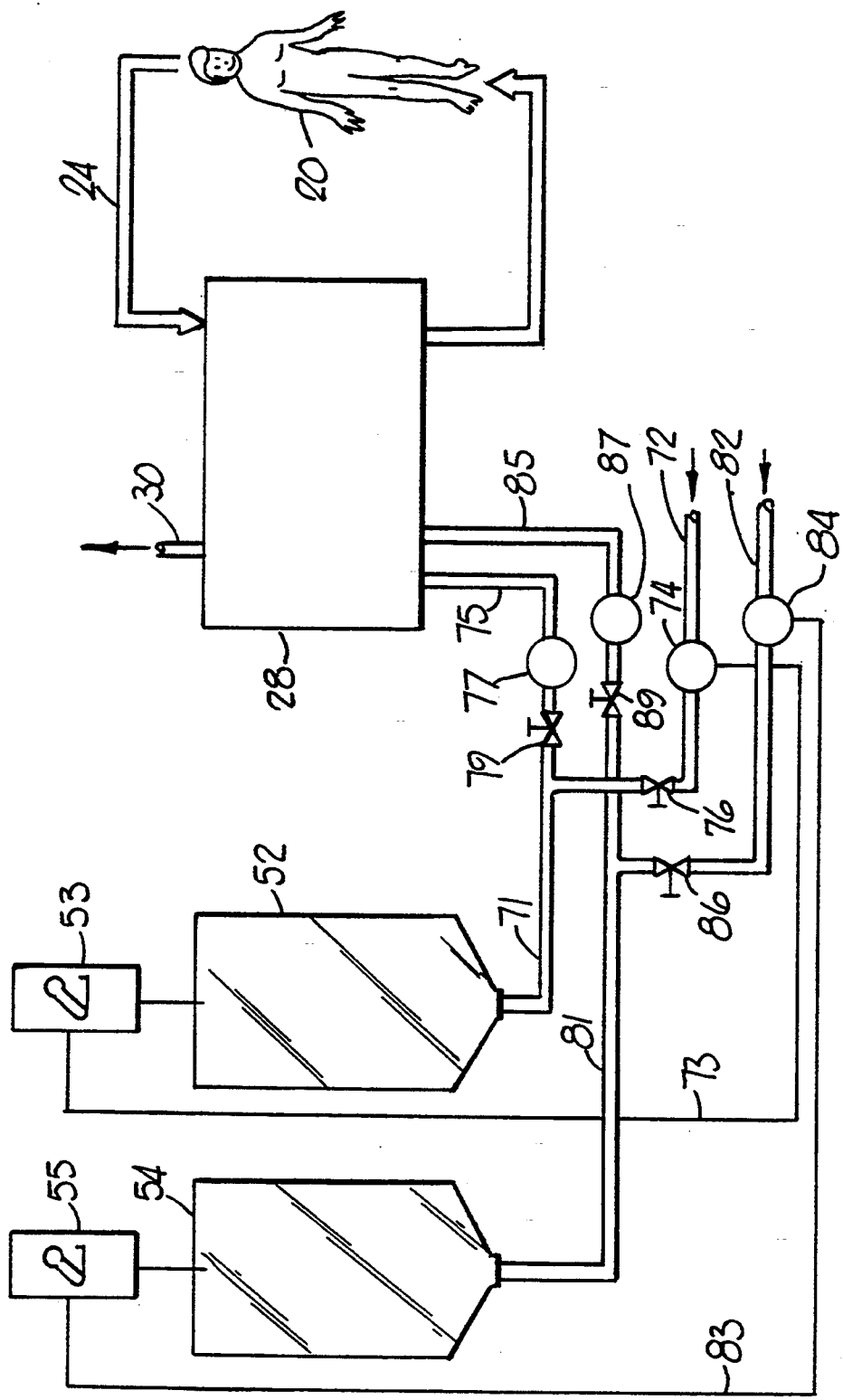
FIG. 1 is a diagrammatic view of a dialysis system for use with the present invention.

A diagrammatic view of the a dialysis system for use with the present invention is shown in FIG. 1. Hemodialysis machines in general are well known in the art and are not described in detail here. Briefly, the vascular system of the patient 20 is a communication with a tubing set 24 which draws blood from the patient, transports it to a dialyzer 28 and returns it to the patient. The dialyzer 28 also receives dialysate. A semipermeable membrane in the dialyzer between the dialysate and the blood allows blood impurities to pass through the membrane into the dialysis solution. The used dialysis solution is discarded through a drain 30.

The present invention relates to the containers for the unused dialysate concentrate. FIG. 1 shows two such containers, one 52 for the acid portion of the dialysate and one 54 for the bicarbonate portion of the dialysate which may also include sodium chloride or other chemicals. The use of bicarbonate as a buffer in hemodialysis is well known. The bicarbonate dialysate is commonly mixed with the acid dialysate just prior to use, to prevent the bicarbonate from precipitating out of the solution during storage. In the preferred embodiment, the acid dialysate container 52 and the bicarbonate dialysate container 54 are essentially identical in configuration and dimensions, although it will be apparent that they could be configured or dimensioned differently without departing from the spirit of the invention. The bicarbonate solution is mixed with the acid solution to form dialysis solution in the dialyzer in the simple diagrammatic view shown in FIG. 1, although the bicarbonate solution may also be mixed with the acid solution in a separate mixing chamber prior to entering the dialyzer or mixed in a dialysate delivery machine.

A set of pumps and valves are used to access the dialysis solution and the bicarbonate solution in the containers 52 and 54. An acid solution water line 72 includes an acid solution inlet pump 74 which allows water to flow from a water source, through an acid solution inlet valve 76 and into the acid dialysate container 52. Similarly, a bicarbonate solution water line 82 includes a bicarbonate solution inlet pump 84 which allows water to flow from a water source, through a bicarbonate solution inlet valve 86 and into the bicarbonate dialysate container 54. An acid solution line 75 allows acid solution to flow from the acid dialysate container 52, through an acid solution outlet valve 79, through an acid solution outlet pump 77, and into the dialyzer 28. Similarly, a bicarbonate solution line 85 allows bicarbonate solution to flow from the bicarbonate dialysate container 54, through a bicarbonate solution outlet valve 89, through a bicarbonate solution outlet pump 87, and into the dialyzer 28. The acid solution water line 72 and acid solution line 75 join to become a single acid line 71 which taps the acid dialysate solution container 52, and the bicarbonate solution water line 82 and the bicarbonate solution line 85 join to become a single bicarbonate line 81 which taps the bicarbonate dialysate container 54.

In operation, the dry bicarbonate and acid dialysate containers 52 and 54 are filled by opening the bicarbonate solution inlet valve 86 and the acid solution inlet valve 76, and activating the acid solution inlet pump 74 and bicarbonate solution inlet pump 84. The pumps 74 and 84 then pump the water into the acid dialysate container 52 and bicarbonate dialysate container 54, respectively, and the water dissolves the concentrated acid and bicarbonate in the manner described below. The pumping of water into the acid dialysate container 52 and the bicarbonate dialysate container 54 continues until the weight of the containers on the trip switches 53 and 55, respectively, deactivate the pumps due to the filling of the containers. After the containers 52 and 54 are filled and the solid concentrate therein is dissolved and the pumps 84 and 74 have been deactivated, the valves 86 and 76 are closed. A microprocessor-based load cell may also be used in lieu of the trip switches.

The acid solution and bicarbonate solution including the dissolved concentrates are then transferred from the containers to the dialyzer 28 or to a dialysate delivery machine by opening the acid solution outlet valve 79 and bicarbonate solution outlet valve 89 and pumping the solutions using the acid solution outlet pump 77 and bicarbonate solution outlet pump 87. After the solutions are mixed appropriately and utilized in the normal manner by the dialyzer, the used solution is discarded through the drain 30.

The acid dialysate container 52 and the bicarbonate dialysate container 54 are mounted such that the filling of the containers can be monitored. In the preferred embodiment, this is accomplished using trip switches 53 and 55 which are in electrical communication with the inlet pumps 84 and 874 through circuits 83 and 73. When the containers 42 and 54 fill sufficiently that the weight of the containers trips the trip switches 53 and 55, a signal is sent to deactivate the pumps 84 and 74 through circuits 83 and 73.

Figure 2:
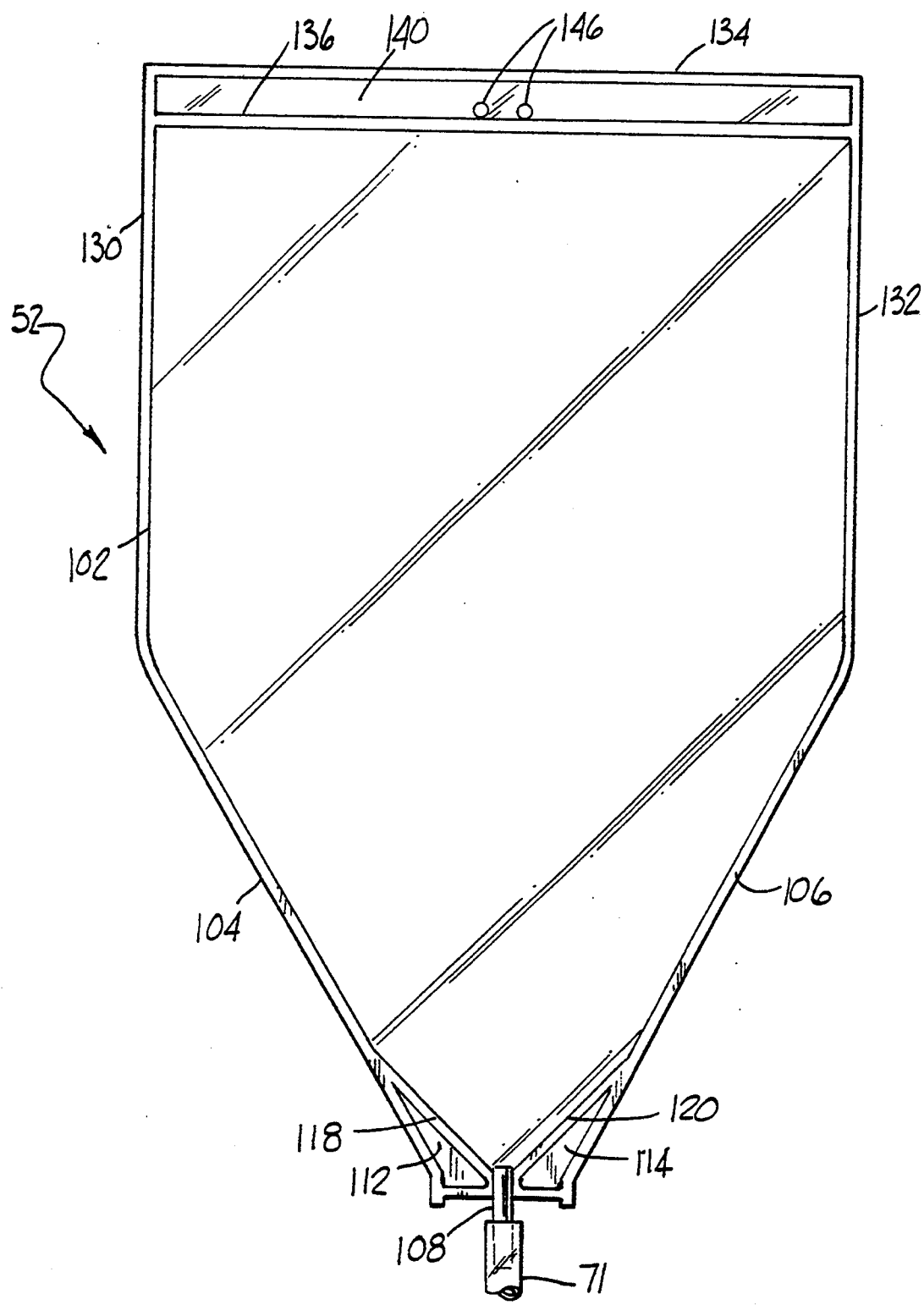
FIG. 2 is a side elevational view of the container of the present invention.

The acid dialysate container 52 without the solid dialysate concentrate, is shown in detail in the side elevational view of FIG. 2. As mentioned above, the bicarbonate dialysate container 54 may be made essentially the same as the acid dialysate container 52, and is not separately described in detail herein. The container 52 is formed in the preferred embodiment from plastic sheet material, specifically a front sheet and a matching back sheet which are welded, heat sealed or adhesively bound to form a peripheral seal 102 around their periphery.

An important aspect to the container 42 is that it be configured to maximize the flow of incoming water through the solid acid dialysate concentrate. In the preferred embodiment, this is accomplished by including inclined sides 204 and 206 which form a V-shaped side in the bottom half of the container 52. At the bottom of this V-shape is the port 108 which joins the dialysis line 71. The port 108 is supported by a left gusset 112 and right gusset 114 formed by the peripheral seal 102 and a left interior seal 118 and right interior seal 120. The port 108 itself is a rigid tube which extends from the interior of the container to the exterior of the container, and is sealed into the container through the peripheral seal 102 and the joining of the left interior seal 118 and right interior seal 120. The peripheral seal 102 is roughly perpendicular to the port 108 where the port 108 enters the container 42, thereby further lending rigidity to the bottom portion of the container so that the dialysis line 71 can be easily connected and disconnected.

The upper half of the container 42 includes roughly vertical sidewalls 130 and 132 extending to a top 134, all of which are bounded by the peripheral seal 102. At the top is also a top interior seal 136 which together with the peripheral seal 102 forms a top gusset 140. Through the gusset extends at least one, and two in the embodiment shown, holes 146 from which the container can be hung.

In the preferred embodiment, the acid dialysate container 42 is of sufficient size to hold approximately 6–8 liters of dialysis solution. Such a volume requires a width between the sidewalls 130 and 132 of about 12 inches, an overall height from the bottom to the top of about 18 inches, and a height from the bottom to the point at which the sidewalls 130 and 132 join the inclined sides 104 and 106 of about 9 inches. The angle between the interior seals 118 and 120 that establish the V-shaped bottom to the interior of the container 42 is approximately 90°.

Figure 3:
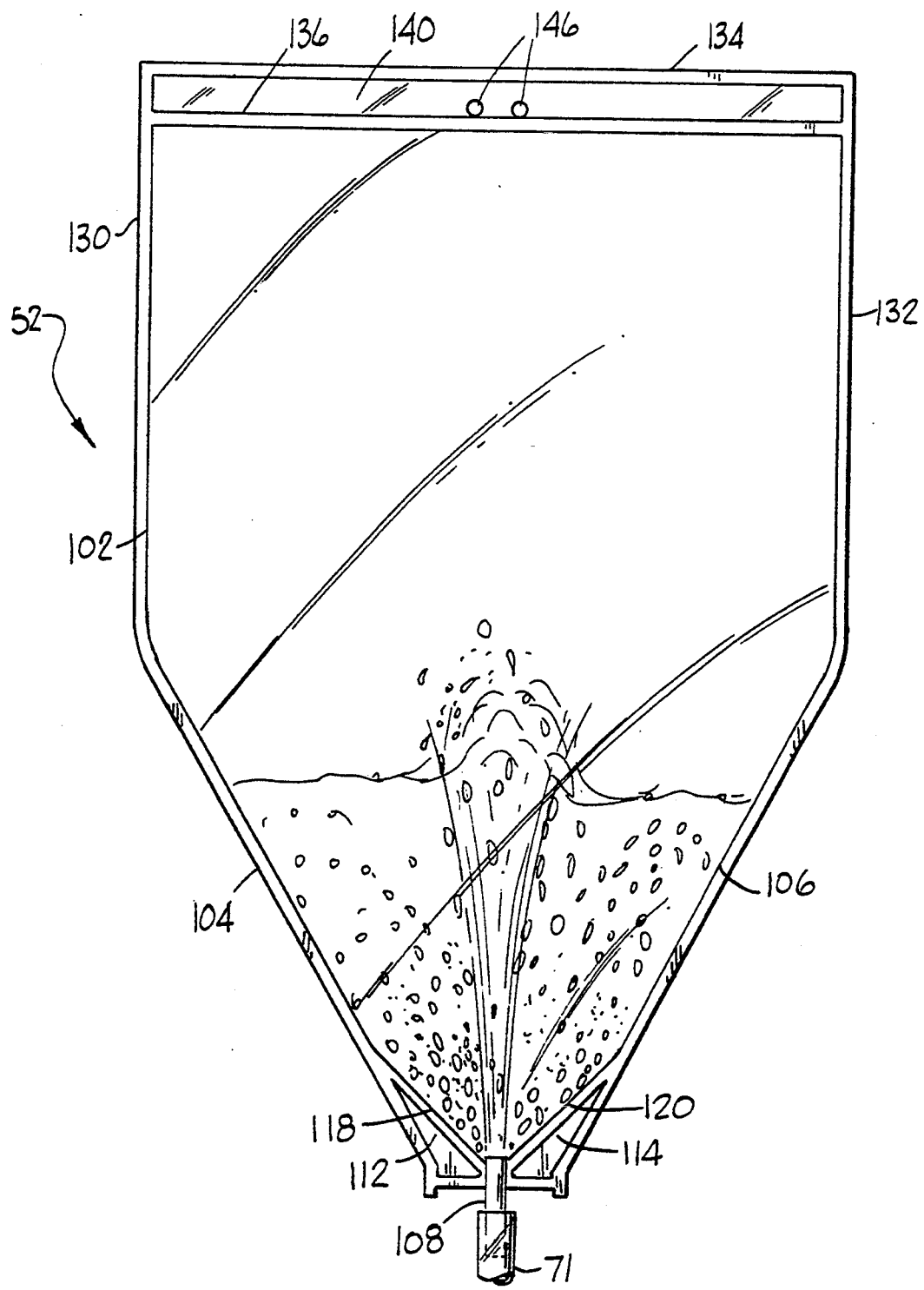
FIG. 3 is a side elevational view of the container of the present invention being filled with water to form a dialysis solution.

In FIG. 3 is shown the container 52 with the solid dialysate concentrate, being filled with water flowing into the container 42 from the dialysis line 71. It can be seen that the water flows through the port 108 and into the container 42 in a turbulent manner which swirls around the granules 180, thereby maximizing the surface area of the granules in contact with the incoming water and the speed of the water passing the granules. Moreover, the granules normally have a specific gravity of greater than one, so they stay toward the bottom of the container as the container gradually fills. The V-shape in the bottom interior ensures that the granules not only stay toward the bottom of the container but also are localized at the port 108 where the water is flowing in so that they stay suspended in the turbulent flow in order to be dissolved.

In the preferred embodiment, the rate of water flow into the dialysis solution container 52 is approximately 1 liter per minute. The 6-8 liter container of the preferred embodiment is thereby filled in approximately 6-8 minutes. It has been found that all the granulated dialysis concentrate dissolves in the 6-8 minutes it takes to fill the container.

We claim:

1. A method for preparing and using a dialysis solution, comprising placing an acid dialysate concentrate into a container, the container having a bottom portion to hold the dialysate concentrate, the bottom portion having a lower end with an access port and the container having a least one side that slopes in relation to an opposite side whereby the container has a width at the lower end that is less than a width above the lower end; sealing the container; flowing water into the container through the access port so that the flowing water produces turbulence in the bottom portion to simultaneously dissolve the dialysate concentrate in the bottom portion; and withdrawing the acid dialysis solution from the container.

2. The method of claim 1, wherein the concentrate is dissolved before the step of flowing water into the container is completed.

3. The method of claim 1, wherein the container with the water has a weight, and the step of flowing water into the container includes monitoring the weight of the container with the water and tripping a switch to discontinue the flow when the weight reaches a known amount.

4. The method of claim 1, wherein the acid dialysate concentrate is a granulated solid.

5. The method of claim 4, wherein the incoming water through the port urges the solid granules upward while the weight of the granules urges the granules downward toward the access port, thereby suspending the granules in the water.

6. The method of claim 1, further comprising placing a bicarbonate dialysate concentrate into a second container, the second container having a bottom portion to hold the bicarbonate concentrate, the bottom portion having a lower end with a second container access port and the second container having at least one side that slopes in relation to an opposite side whereby the second container has a width at the lower end that is less than a width above the lower end; sealing the second container; flowing water into the second container through the second container access port so that the flowing water produces a turbulence in the bottom portion to simultaneously dissolve the bicarbonate concentrate in the bottom portion; withdrawing the bicarbonate dialysis solution from the second container through the second container access port; and mixing the acid dialysis solution with the bicarbonate dialysis solution.

7. The method of claim 6, wherein the bicarbonate dialysate concentrate includes sodium chloride.

* * * * *